United States Patent
Fercher et al.

(10) Patent No.: US 6,788,421 B2
(45) Date of Patent: Sep. 7, 2004

(54) ARRANGEMENTS FOR COHERENCE TOPOGRAPHIC RAY TRACING ON THE EYE

(75) Inventors: Adolf Friedrich Fercher, Vienna (AT); Roland Barth, Jena (DE)

(73) Assignee: Carl Zeiss Jena GmbH, Jena (DE)

(*) Notice: Subject to any disclaimer, the term of this patent is extended or adjusted under 35 U.S.C. 154(b) by 0 days.

(21) Appl. No.: 10/167,130

(22) Filed: Jun. 10, 2002

(65) Prior Publication Data
US 2003/0053072 A1 Mar. 20, 2003

(30) Foreign Application Priority Data
Jun. 11, 2001 (DE) ............................... 101 28 219

(51) Int. Cl.⁷ ................................................. G01B 9/02
(52) U.S. Cl. ...................................................... 356/497
(58) Field of Search .............................. 356/479, 496, 356/497, 503, 505

(56) References Cited

U.S. PATENT DOCUMENTS 5,459,570 A * 10/1995 Swanson et al. ............ 356/479
5,719,673 A * 2/1998 Dorsel et al. ............... 356/503
6,307,634 B2 * 10/2001 Hitzenberger et al. ...... 356/484

* cited by examiner

Primary Examiner—Samuel A. Turner
Assistant Examiner—Michael A. Lyons
(74) Attorney, Agent, or Firm—Reed Smith LLP

(57) ABSTRACT

Topographic measurement of eye structures based on short coherence interferometry is the subject of the invention. The problem occurring in this connection is that longitudinal and transverse eye movements during signal registration lead to errors in the measured structure. The influences of longitudinal eye movements are compensated in that the reference beam, independent from the measurement beam, is directed to the corneal vertex and is reflected at the latter. The influences of longitudinal eye movements are minimized in that the transverse position of the eye is monitored by means of a direction-dependent registration of the light reflected at the corneal vertex by means of a diode array or a four-quadrant diode and transverse misalignment is detected and compensated.

5 Claims, 3 Drawing Sheets

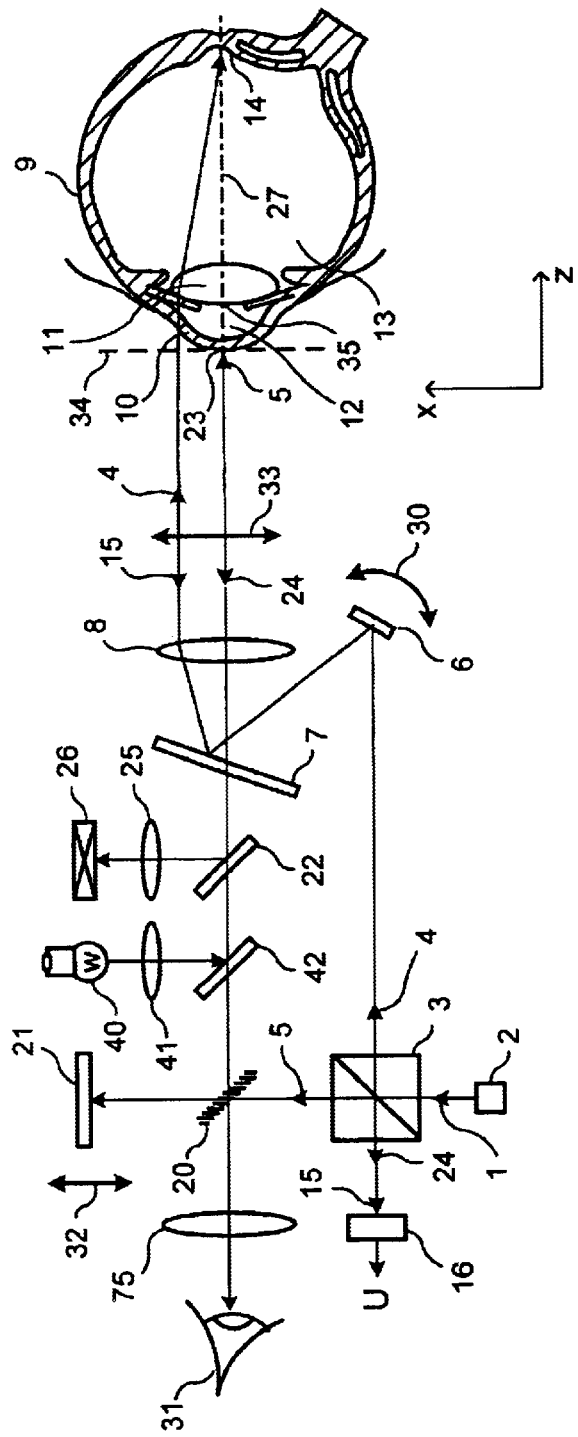
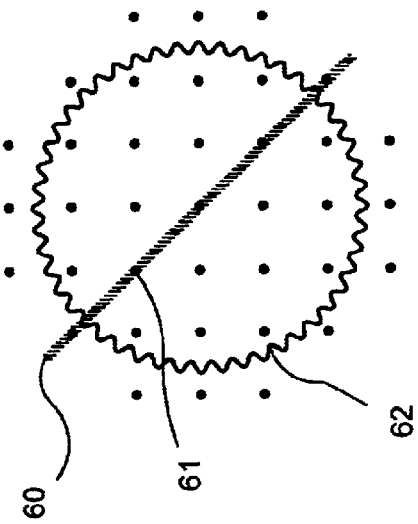
FIG. 1
FIG. 2

ARRANGEMENTS FOR COHERENCE TOPOGRAPHIC RAY TRACING ON THE EYE

CROSS-REFERENCE TO RELATED APPLICATIONS

This application claims German Application No. 101 28 219.2, filed Jun. 11, 2001, the complete disclosure of which is hereby incorporated by reference.

BACKGROUND OF THE INVENTION a) Field of the Invention

The invention is directed to topographic measurement of eye structures such as the cornea and lens in ophthalmology.

b) Description of the Related Art

As the result of new developments in ophthalmology which are characterized by many different types of surgical procedures on the lens of the eye (e.g., cataract surgery) and on the cornea (refractive cornea surgery), there is a considerable demand for measurement methods which quantify the entire structure of the eye topographically. While several methods known under the heading of ray tracing can determine the modulation transfer function and accordingly also the point spread function of the eye [for example, R. Navarro, E. Moreno, C. Dorronsoro, *J. Opt. Soc. Am.*, Vol. 15 (1998): 2521–2529], these methods only measure the total effect of all optical components of the eye and do not provide any information about the influences of the individual components of the eye and particularly about the exact geometry of these components. However, in order to analyze what ophthalmologic procedure has what effect on the eye or, conversely, what influence is exerted by what optic component of the eye, it is necessary to know the exact geometry of all optically active components. For this purpose, the topography of the intraocular boundary surfaces must be measured.

Coherence topograms, described in A. F. Fercher and C. K. Hitzenberger in *Springer Series in Optical Sciences* (ed. T. Asakura), Vol. 4, Springer Verlag, Berlin 1999, are a suitable optical method for this purpose. Optical coherence topograms are obtained from a series of z-signals measured in longitudinal direction by short coherence interferometry from object areas which are adjacent in transverse x-direction by scanning the optical length of the reference arm of a two-beam interferometer. In the method described in the literature cited above, the measurement beam and reference beam always extend coaxially and centrally through the pupil of the eye. Therefore, it can only be used to acquire the geometry of the fundus, but not for partial length topography of the entire eye. Further, measurement errors are caused by transverse misalignments transverse to the axis of the eye during signal registration.

Another optical method which is suitable for this purpose is described in J. A. Izatt, M. R. Hee, D. Huang, J. G. Fujimoto, E. A. Swanson, C. P. Lin, J. S. Schuman, C. A Puliafito, *SPIE Proc.,* 1877 (1993): 136–144. This relates to the method of optical coherence tomography (OCT). However, this method fundamentally suffers from the problem that eye movements during signal registration lead to errors in the measured structure. In particular, longitudinal movements in direction of the axis of the eye cause a falsification of the depth position or z-position of the measured structures.

OBJECT AND SUMMARY OF THE INVENTION

Therefore, it is the primary object of the invention to provide arrangements for coherence topography of the eye by means of a series of depth signals which are measured by means of short coherence interferometry in different pupil points by scanning the optical length of the reference arm of a two-beam interferometer, wherein longitudinal movements in direction of the axis of the eye and transverse movements transverse to the axis of the eye do not cause a falsifying of the positions of the measured structures, and longitudinal depth signals or z-signals can be obtained at selected points in the pupil of the eye also outside of the visual axis.

This object is met in that the measurement beam of a short coherence interferometer is radiated into the pupil of the eye in a series of measurement positions and the reference beam, independent from the measurement beam, is fixedly directed to the corneal vertex and reflected at the latter. Every longitudinal movement of the eye then leads to the same phase displacement in the reference beam as in the measurement beam and has no effect on the short coherence interferometry. Further, the transverse position of the eye is monitored by means of a direction-dependent registration of the light reflected at the corneal vertex by means of a diode array or a four-quadrant diode and a criterion is obtained for the transverse alignment of the eye with respect to the beam axis. Transverse misalignments can be detected and compensated in this way. Finally, a pair of deflecting mirrors whose axes of rotation are oriented normal to one another is used for controlling the measurement beam at selected pupil points.

In the following, the invention will be described with reference to the figures.

BRIEF DESCRIPTION OF THE DRAWINGS

In the drawings:

FIG. 1 describes the basic method according to the invention;

FIG. 2 shows an equidistant arrangement of measurement points on the eye;

DESCRIPTION OF THE PREFERRED EMBODIMENTS

Figure 3:
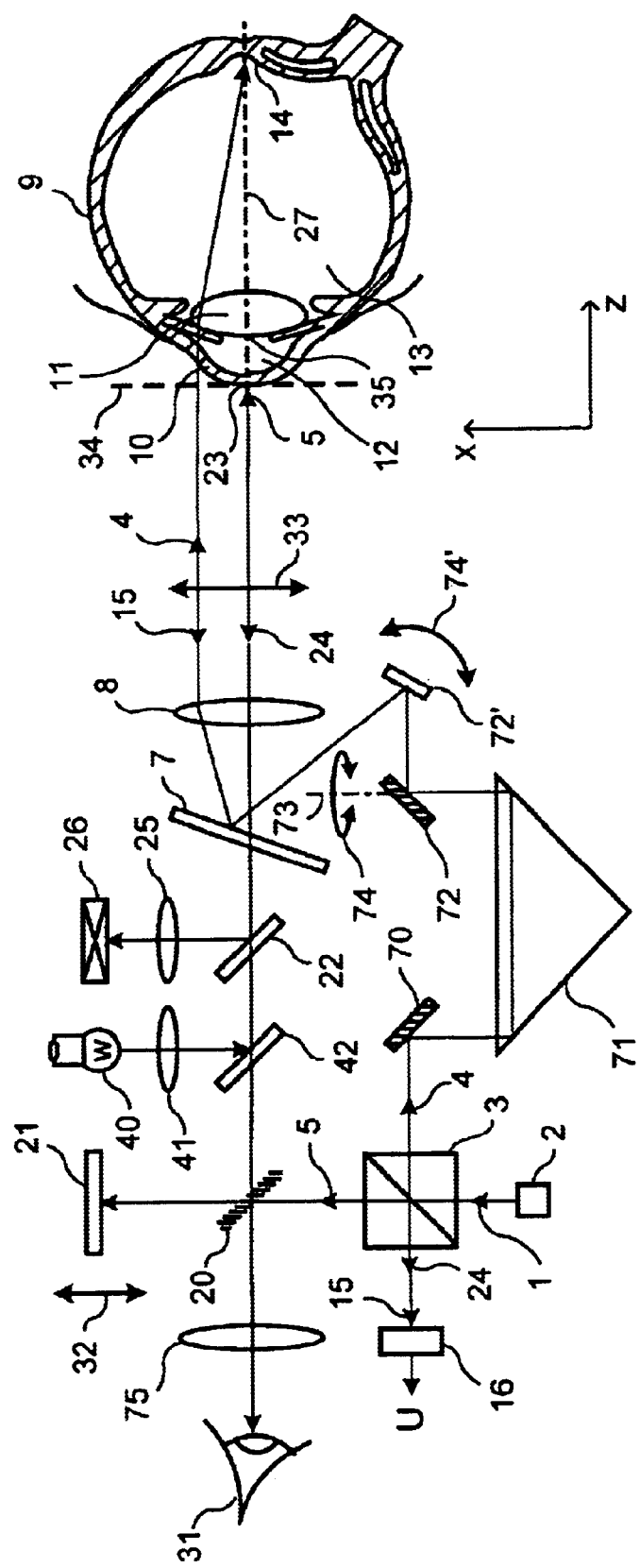
FIG. 3 describes how the measurement beam can be controlled at different points on the pupil of the eye.

FIG. 1 shows the beam path of the topographic short coherence interferometer. The light beam 1 of a partial temporal coherent light source 2, for example, a superluminescent diode, illuminates the interferometer. This light beam is divided into measurement beam 4 and reference beam 5 at the beam splitter 3. The measurement beam 4 is deflected by the rotating or oscillating (double-arrow 30) deflecting mirror 6 to the partially reflecting plate 7 and then through the objective 8 to the eye 9. The deflecting mirror 6 is located in the focal plane of the optics 8. In the eye, this light beam is directed through various tissue such as the cornea 10 and lens 11 through the aqueous humour 12 and the vitreous body 13 to the ocular fundus 14. Light which is backscattered in the direction of the incident measurement beam 4 by this tissue and its boundary surfaces and by the ocular fundus takes, as light beam 15, the same path as the measurement beam 4 up until the beam splitter 3, but in the opposite direction. The returning light beam 15 penetrates the beam splitter 3 and strikes the photodetector 16. The longitudinal depth positions of the light-reemitting locations are determined from the photoelectric signal U of the photodetector 16 by known methods of short coherence interferometry.

When a short coherent light source emitting short-wave light (e.g., blue-radiating laser diode) is used in the two-beam interferometer instead of the conventional superluminescent diode mentioned above, the light components (that is, light beam 15) which are reemitted by the intraocular tissues, i.e., the cornea 10, lens 11, vitreous body 13 and ocular fundus 14, are appreciably more pronounced. Since the signals obtained at the photodetector 16 have a greater amplitude, a more precise interferometric depth determination of the light-reemitting layers is possible.

The reference beam 5 passes through the beam splitter 20, is reflected by the reference mirror 21 and is then directed from beam splitter 20 through beam splitters 42 and 22 and the partially reflecting plate 7 and is focused on the corneal vertex 23 by the objective 8. The light bundle 24 reflected at the corneal vertex 23 travels back along the same path as the reference beam 5 and is reflected by the beam splitter 3 onto the photodetector 16. Further, a portion of this light bundle passes through the beam splitter 20 in a straight line and then through a lens 75 to allow the observer 31 to visually monitor the centering of the eye with respect to the axis of the reference beam 5.

In short coherence interferometry, the optical path length of the reference beam 5 is scanned; that is, during the "z-scan", as it is called, the reference mirror 21 is moved along the axis of the reference beam 5 in the direction indicated by the double-arrow 32. When the path length of the reference beam 5 from the beam splitter 3 to the corneal vertex 23 and back within the coherence length $I_c$ of the light beam 1 is equal to the path length of the measurement beam 4 from the beam splitter 3 to a light-reemitting location in the eye 9 and back to the beam splitter 3, interference occurs at the photodetector 16. By continuously displacing the reference mirror 21, the z-position of light-reemitting locations in the object is registered by means of the interference occurring at the photodetector 16. The z-position is determined with an accuracy given approximately by the coherence length $$I_c \cong \frac{\lambda^2}{\Delta\lambda}$$

of the utilized light, where $\lambda$ is the average wavelength and $\Delta\lambda$ is the wavelength bandwidth of the utilized radiation. In order to acquire the x-coordinate, either the object is moved in x-direction or, as is indicated in FIG. 1, the measurement beam scans the x-coordinates at the object 1 by means of a rotating or oscillating rotating mirror 6. The measurement beam 4 is accordingly moved normal to the visual axis 27 of the eye (double-arrow 33).

The light bundle 24 returning from the corneal vertex is reflected by the beam splitter 22 to the optics 25. The optics 25, together with optics 8, project an image of the light spot generated on the corneal vertex 23 by the reference beam 5 onto a diode array, for example, a four-quadrant diode 26. In this way, a direction-sensitive registration of the light bundle reflected at the cornea is obtained.

When the reference beam 5 is located on the visual axis 27 of the eye, a rotation-symmetric light spot occurs on the diode array. When the reference beam 5 is located outside of the optic axis 27 of the eye, it is reflected more laterally in a corresponding manner and the brightness distribution in the light spot on the photodetector array 26 deviates from the rotational symmetry of the eye. The centering of the eye with reference to the axis of the reference beam 5 can be assessed based on the value of the signal of the diode array. These signals can then be used for readjusting the centering, for example, by displacing the interferometer relative to the eye and/or the registration of the z-signals measured by short coherence interferometry can be interrupted when a threshold value is exceeded. In this way, measurement errors due to transverse misalignment of the eye can be drastically reduced. It is noted that instead of the reference beam 5 another light beam which is reflected in coaxial to the reference beam could also be reflected in for readjustment of centering. A light beam of this kind can be generated by a lamp 40, collimated through optics 41 and reflected in coaxial to the axis of the reference beam 5 by means of a beam splitter 42.

Longitudinal movements in direction of the axis of the eye which lead to falsified z-positions of the measured structures are compensated by the arrangement according to the invention because the reference beam 5 is reflected at the corneal vertex. In this case, every longitudinal movement of the eye leads to the same phase displacement in the reference beam as in the measurement beam. This also simplifies the interpretation of the measured object structure: all z-signals measured by short coherence interferometry have their reference point in a plane 34 tangential to the corneal vertex 23.

The topographic data acquisition at the eye can be carried out in two dimensions or in three dimensions. In two-dimensional data acquisition, the measurement positions can be equidistant along a straight line, for example, along a pupil diameter, as is indicated in FIG. 2 by the points 61 lying on the straight line 60. The edge of the pupil is indicated by 62. This results in topograms corresponding to FIG. 1 in A. F. Fercher and C. K. Hitzenberger, *Springer Series in Optical Sciences* (ed. T. Asakura), Vol. 4, Springer Verlag, Berlin 1999. For three-dimensional data acquisition, the measurement positions in the entire pupil surface (x- and y-coordinates) can be distributed in an equidistant manner, for example, or can be distributed over the pupil in a comb-shaped or wavy manner. The three-dimensional coordinates of the cornea surfaces and lens surfaces are then obtained together with the z-coordinates of short coherence interferometry. In order to implement topographic data acquisition in this manner, it must be possible to control the measurement beam at selected locations on the (two-dimensional) pupil. As is described in FIG. 3, this is possible by means of a pair of scanning mirrors 72 and 72' whose axes of rotation extend normal to one another. In FIG. 3, for example, the axis of rotation of mirror 72 lies in the drawing plane and the axis of rotation of mirror 72' is oriented normal to the drawing plane.

Figure 4:
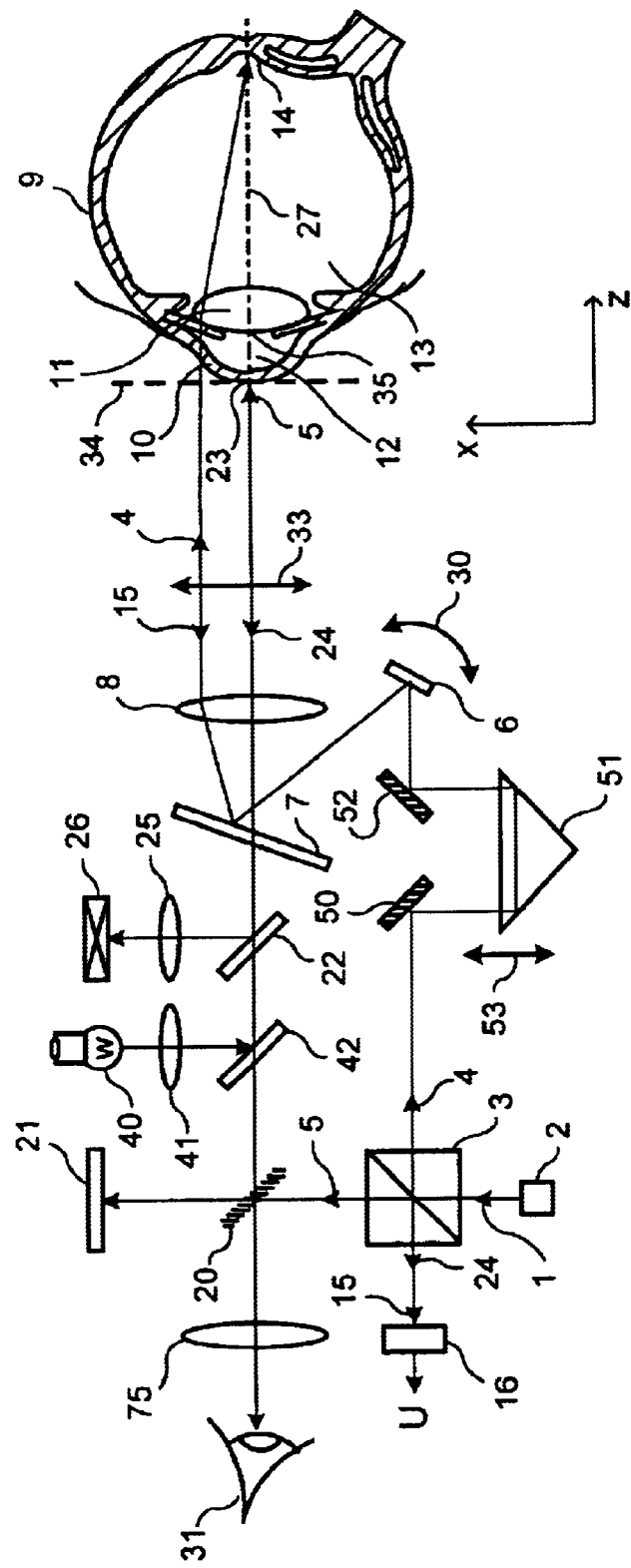
FIG. 4 describes an alternative in which the scanning of the optical length of the reference beam is replaced by the scanning of the optical length of the object beam.

Finally, it is noted that the scanning of the reference beam can also be carried out in another way other than by the moving mirror 21, for example, by arrangements such as those described in Application A 472/99, "Periodically operating optical path length modulator". The scanning of the optical length of the reference arm can also be replaced by scanning the optical length of the measurement arm, as is shown in FIG. 4. In this case, the measurement beam 4 is reflected to a roof prism 51 by a deflecting mirror 50 and is reflected back from the roof prism 51 via the deflecting mirror 52 to the deflecting mirror 6. In this case, the scanning of the optical length of the measurement arm is carried out by moving the roof prism 51 in the direction indicated by the double-arrow 53.

Another advantageous embodiment form of the invention consists in the use of a short coherent light source 2 emitting short-wave light in the two-beam interferometer (e.g., blue-radiating laser diode). Accordingly, the light components (that is, light beam 15) which are reemitted by the intraocular tissues, i.e., the cornea 10, lens 11, vitreous body 13 and ocular fundus 14, are appreciably more pronounced than in conventional short coherence interferometers which use light sources in the near infrared range according to the prior art. Since the signals obtained in this way have a greater amplitude, a more precise detection and, therefore, more precise interferometric depth determination of the light-reemitting layers is possible.

While the foregoing description and drawings represent the present invention, it will be obvious to those skilled in the art that various changes may be made therein without departing from the true spirit and scope of the present invention.

Reference Numbers

| | |
|---|---|
| 1 | partially coherent light beam |
| 2 | short coherence light source |
| 3 | beam splitter |
| 4 | measurement beam |
| 5 | reference beam |
| 6 | rotating or oscillating deflecting mirror |
| 7 | partially reflecting plate |
| 8 | objective |
| 9 | eye |
| 10 | cornea |
| 11 | eye lens |
| 12 | aqueous humour |
| 13 | vitreous body |
| 14 | ocular fundus |
| 15 | reemitted measurement beam |
| 16 | photodetector |
| 20 | beam splitter |
| 21 | reference mirror |
| 22 | beam splitter |
| 23 | corneal vertex |
| 24 | reflected reference beam |
| 25 | optics |
| 26 | detector array, four-quadrant diode |
| 27 | visual axis of the eye |
| 30 | movement direction of the rotating or oscillating deflecting mirror |
| 31 | observer |
| 32 | movement direction of the reference mirror |
| 33 | movement direction of the measurement beam |
| 34 | plane tangent to the corneal vertex |
| 40 | light source |
| 41 | optics |
| 42 | beam splitter |
| 50 | deflecting mirror |
| 51 | roof prism |
| 52 | deflecting mirror |
| 53 | movement direction of the roof prism |
| 70 | deflecting mirror |
| 71 | roof prism |
| 72 and 72' | pair of rotating mirrors |
| 73 | axis of rotation of the rotating mirror 72 |
| 74 and 74' | rotating movements of the pair of rotating mirrors 72 and 72' |

What is claimed is:

1. An arrangement for coherence topography of the eye by a series of depth signals which are measured by short coherence interferometry in different pupil points by scanning an optical length of a reference arm of a two-beam interferometer, comprising that:

a first device that radiates a measurement beam of a short coherence interferometer into the pupil of an eye in a series of measurement positions; and a second device that fixedly directs a reference beam, independent from the measurement beam, to the corneal vertex, the reference beam being reflected at the corneal vertex.

2. The arrangement according to claim 1, further comprising a diode array or four-quadrant diode that monitors the position of the eye transverse to a depth position of the eye by a direction-dependent registration of the light reflected at the corneal vertex and a criterion is obtained for the transverse alignment of the eye with respect to the beam axis.

3. The arrangement according to claim 1, wherein the short coherent interferometer radiates short-wave light.

4. An arrangement for coherence topography of an eye by a series of depth signals that are measured by short coherence interferometry in different pupil points by scanning an optical length of a reference arm of a two-beam interferometer, comprising:

a first light source that provides a short wave measurement beam below an NIR range;

a second light source that provides a reference beam;

a first device that guides the measurement beam into the pupil of the eye at a series of measurement positions; and a second device that fixedly directs the reference beam, independent from the measurement beam, to the corneal vertex which is reflected at the corneal vertex; and a detector that receives both the reflected reference beam and the measurement beam returning from the eye.

5. The arrangement according to claim 4, wherein a single source generates both the reference beam and the measurement beam.

* * * * *